United States Patent
Knebel et al.

(10) Patent No.: US 10,458,899 B2
(45) Date of Patent: Oct. 29, 2019

(54) METHOD AND OPTICAL DEVICE FOR MICROSCOPICALLY EXAMINING A MULTIPLICITY OF SPECIMENS

(71) Applicant: Leica Microsystems CMS GmbH, Wetzlar (DE)

(72) Inventors: Werner Knebel, Kronau (DE); Wernher Fouquet, Mannheim (DE); Frank Sieckmann, Eppingen (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 300 days.

(21) Appl. No.: 14/899,157

(22) PCT Filed: Jun. 18, 2014

(86) PCT No.: PCT/EP2014/062907
§ 371 (c)(1),
(2) Date: Dec. 17, 2015

(87) PCT Pub. No.: WO2014/202704
PCT Pub. Date: Dec. 24, 2014

(65) Prior Publication Data
US 2016/0153892 A1 Jun. 2, 2016

(30) Foreign Application Priority Data

Jun. 18, 2013 (DE) .......................... 10 2013 211426

(51) Int. Cl.
*G02B 21/06* (2006.01)
*G01N 21/13* (2006.01)
(Continued)

(52) U.S. Cl.
CPC ......... *G01N 21/13* (2013.01); *G02B 21/0024* (2013.01); *G02B 21/0032* (2013.01);
(Continued)

(58) Field of Classification Search
CPC ...... G02B 21/06; A61B 5/150251; A61B 1/00
(Continued)

(56) References Cited

U.S. PATENT DOCUMENTS

| | | |
|---|---|---|
| 2003/0002148 A1 | 1/2003 | Engelhardt |
| 2006/0012866 A1 | 1/2006 | Wolleschensky |

(Continued)

FOREIGN PATENT DOCUMENTS

| | | |
|---|---|---|
| EP | 0350189 A2 | 1/1990 |
| WO | 2005/036451 A1 | 4/2005 |

(Continued)

OTHER PUBLICATIONS

Bruns, Thomas et al., Preparation strategy and illumination of three-dimensional cell cultures in light sheet-based fluorescence microscopy, Oct. 2012, Journal of Biomedical Optics, vol. 17(10), pp. 101518-1 to 101518-5.

(Continued)

*Primary Examiner* — William R Alexander
*Assistant Examiner* — Tamara Y. Washington
(74) *Attorney, Agent, or Firm* — Hodgson Russ LLP

(57) ABSTRACT

The invention relates to a method for microscopic investigation of a plurality of samples. The method contains the step of arranging the samples in a sample holder that is movable, in particular in motorized and/or automatic fashion, relative to a sample illumination position in such a way that at least one of the samples is respectively successively positionable in the sample illumination position, a clearance for a deflection means respectively remaining adjacent to the sample that is currently located in the sample illumination position; the step of focusing a light stripe with an illumination objective; the step of deflecting the light stripe, once it has passed through the illumination objective, with the deflection means in such a way that the light stripe propa- (Continued)

gates at an angle different from zero degrees with respect to the optical axis of the illumination objective and has a focus in the sample illumination position; and the step of successively positioning the samples, retained with the sample holder, in the sample illumination position, and detecting the detected light emerging from the sample respectively located in the sample illumination position. The invention furthermore relates to an optical apparatus having a sample holder that holds a plurality of samples and is supported movably, in particular in motorized and/or automatic fashion, relative to a sample illumination position in such a way that at least one of the samples is respectively successively positionable in the sample illumination position.

27 Claims, 10 Drawing Sheets

(51) Int. Cl.
G02B 21/00 (2006.01)
G02B 21/34 (2006.01)
G02B 21/36 (2006.01)
G02B 21/26 (2006.01)

(52) U.S. Cl.
CPC ......... *G02B 21/0076* (2013.01); *G02B 21/06* (2013.01); *G02B 21/26* (2013.01); *G02B 21/34* (2013.01); *G02B 21/367* (2013.01); *G01N 2021/135* (2013.01)

(58) Field of Classification Search
USPC .................................................. 359/368–398
See application file for complete search history.

(56) References Cited

U.S. PATENT DOCUMENTS

| | | |
|---|---|---|
| 2007/0109633 A1 | 5/2007 | Stelzer |
| 2013/0107358 A1* | 5/2013 | Knebel .............. G02B 21/0032 359/385 |
| 2013/0315802 A1* | 11/2013 | Manian ................. B01L 3/5027 422/563 |
| 2013/0335818 A1* | 12/2013 | Knebel .............. G01N 21/6458 359/385 |

FOREIGN PATENT DOCUMENTS

| | | |
|---|---|---|
| WO | 2007/065711 A1 | 6/2007 |
| WO | 2012/122027 A2 | 9/2012 |

OTHER PUBLICATIONS

Yanik, Mehmet Fatih et al., Technologies for Micromanipulating, Imaging, and Phenotyping Small Invertebrates and Vertebrates, Sep. 2011, Annual Review of Biomedical Engineering, vol. 13, pp. 185 to 217.

* cited by examiner

METHOD AND OPTICAL DEVICE FOR MICROSCOPICALLY EXAMINING A MULTIPLICITY OF SPECIMENS

CROSS-REFERENCE TO RELATED APPLICATIONS

The present application is the U.S. national phase of International Application No. PCT/EP2014/062907 filed Jun. 18, 2014, which claims priority of German Application No. 10 2013 211 426.5 filed Jun. 18, 2013, the entirety of which is incorporated herein by reference.

FIELD OF THE INVENTION

The invention relates to a method for microscopic investigation of a plurality of samples.

BACKGROUND OF THE INVENTION

The invention furthermore relates to an optical apparatus for microscopic investigation of a plurality of samples, having a sample holder that holds a plurality of samples and is supported movably, in particular in motorized and/or automatic fashion, relative to a sample illumination position in such a way that at least one of the samples is respectively successively positionable in the sample illumination position.

The need exists in some applications, for example for particular serial investigations or statistical investigations, to microscopically investigate a plurality of samples in succession, rapidly and preferably automatically. DE 199 50 225 A 1, for example, discloses a particular arrangement for allowing a large number of specific detection regions, which are distributed in grid fashion on a carrier of up to 22×60 mm, to be scanned with a confocal scanning microscope. According to the teaching of this document, the problem that the carrier is substantially larger than the object field of a usual scanning microscope is solved with the aid of an arm, pivotable in a plane parallel to the carrier, that carries some of the optical components.

Such a solution is not only very complex but also has the disadvantage that three-dimensional imaging of a plurality of samples would still take a very long time; this is not acceptable in particular with usually lifetime-limited, light-sensitive samples.

Many samples to be investigated microscopically have a limited lifetime. The reason for this circumstance is often, among others, their light-sensitivity. Three-dimensional scanning, for example using a scanning microscope, of samples arranged, for example, in the form of a matrix on a specimen slide is in this regard problematic in practice, since the scanning operation requires a great deal of time, and sample regions that lie outside the currently relevant scanning point are also respectively impinged upon by illumination light during the scanning operation and thereby damaged.

An entirely different technology, in which the sample is illuminated in layers, in principle allows more rapid acquisition of image data with less impact on samples, but hitherto has not been suitable for rapid mass investigations of samples, because the optical apparatuses required are technically very complex and because the samples must be separately and individually arranged in particular apparatuses and the observation apparatus must be laboriously configured individually for each sample. This method is known in particular as single plane illumination microscopy (SPIM).

A microscope operating with the SPIM method is described in DE 102 57 423 A1. With this microscope, a sample is illuminated with a thin light stripe while observation occurs perpendicularly to the plane of the illuminating light stripe. Illumination and detection occur here via two separate optical beam paths each having a separate optical system, in particular having two separate, mutually perpendicular objectives. The light stripe is generated by an illumination objective and a cylindrical optic preceding it. For image acquisition, the sample is moved through the light stripe that is stationary with respect to the detector, in order to acquire fluorescent light and/or scattered light in layers with a planar detector. The layer image data thereby obtained can then be assembled into a data set corresponding to a three-dimensional image of the sample.

In particular, this method as a rule cannot be implemented using apparatuses that have a conventional microscope structure with a standard microscope stand. Complex and expensive special arrangements are instead needed in order to implement these techniques.

DE 10 2004 034 957 A1 discloses an arrangement for microscopic observation of a sample via a microscope objective in whose housing light guides are provided, outside the lens optic, for the illumination light to the sample. The illumination light initially proceeds parallel to the optical axis of the objective inside the light guide, and then encounters an annular reflector of small aperture, attached to the objective housing, that focuses the illumination light with the aid of additional imaging elements into the sample, perpendicularly to the optical axis of the microscope objective and thus perpendicularly to the observation direction. Here as well, the sample is illuminated in area fashion using the SPIM principle. With this embodiment, positioning the sample inside the annular reflector is particularly problematic. An apparatus of this kind is therefore unsuitable for utilization of an automated method for serial investigation of a plurality of samples.

It is also known, especially for the investigation of aquatic organisms, not to hold the samples with a sample holder but instead to aspirate them through a glass capillary that is transilluminated with a light sheet. A procedure of this kind is known, for example, from the article by Burns et al., "Preparation strategy and illumination of three-dimensional cell cultures in light sheet-based fluorescence microscopy," Journal of Biomedical Optics, Vol. 17(19), 101518 (October 2012). A procedure of this kind is unsuitable for structured, systematic, and targeted microscopic investigation of a plurality of samples. The article by Yanik et al., "Technologies for Micromanipulating, Imaging, and Phenotyping Small Invertebrates and Vertebrates," Annu. Rev. Biomed. Eng. 2011; 13:185-217, also discloses a method in which the samples are pumped through a capillary.

SUMMARY OF THE INVENTION

The object of the present invention is therefore to describe a method that allows a microscopic investigation of a plurality of samples to be undertaken with low sample impact, efficiently, precisely, and preferably in automated fashion.

The object is achieved by a method that is characterized by the following steps:

a. arranging the samples in a sample holder that is movable, in particular in motorized and/or automatic fashion, relative to a sample illumination position in such a way that at least one of the samples is respectively successively positionable in the sample illumination position, a clearance for a deflection means respectively remaining adjacent to the sample that is currently located in the sample illumination position;

b. focusing a light stripe with an illumination objective;

c. deflecting the light stripe, once it has passed through the illumination objective, with the deflection means in such a way that the light stripe propagates at an angle different from zero degrees, in particular at an angle greater than 10 degrees, very particularly at a right angle, with respect to the optical axis of the illumination objective, and has a focus in the sample illumination position; and d. successively positioning the samples, retained with the sample holder, in the sample illumination position, and detecting the detected light emerging from the sample respectively located in the sample illumination position.

A further object of the present invention is to describe an apparatus that allows a microscopic investigation of a plurality of samples to be undertaken with low sample impact, efficiently, precisely, and preferably in automated fashion.

This object is achieved by an apparatus that is characterized in that a clearance for a deflection means is present respectively adjacent to the sample that is currently located in the sample illumination position, said means deflecting the light stripe emerging from an illumination objective to the illumination position in such a way that the light stripe propagates at an angle different from zero degrees, in particular at a right angle, with respect to the optical axis of the illumination objective; and having a detector that detects the detected light emerging from the sample respectively located in the sample illumination position.

The invention makes it possible to perform a mass investigation of light-sensitive samples, for example living cell aggregates such as tissue cultures of skin cells, and the embryonic development of vertebrates, with high image contrast and low phototoxicity. A high throughput of samples per unit time is also made possible with no need to accept degradation in terms of the aforementioned parameters. In particular, the present invention advantageously allows an automated mass investigation to be performed, assisted in particular by the utilization according to the present invention of SPIM technology in conjunction with the arrangement and use of the sample holder, and the particular beam guidance relative to the samples, according to the present invention.

For example, the samples can be held with the sample holder in matrix form and/or in a common plane. A sample arrangement of this kind enables rapid and precise successive switching of the samples into the sample illumination position using simple displacement motions.

Alternatively or additionally, provision can also be made for the samples to be held with the sample holder in at least one straight row. With this kind of embodiment, a displacement motion in a single direction is sufficient to convey the samples successively into the sample illumination position.

Alternatively, the samples can be held with the sample holder in a curved row, in particular in an annular row. Provision can be made in particular that the sample holder is embodied as a revolving turret. With these embodiments, the samples can be successively conveyed into the sample illumination position by respectively executing a rotary motion.

In a particular embodiment one or more of the samples are retained in at least one sub-holder of the sample holder. Provision can be made in particular that the sample holder comprises multiple, in particular strand-shaped, sub-holders. The sub-holder or sub-holders can advantageously be arranged in a vessel, in particular open at the top, that is filled with an immersion liquid, in particular in such a way that the samples and/or the sub-holder are submerged, preferably completely, in the immersion liquid. Upon investigation of the samples, a detection objective that in particular can also carry the deflection means can dip into the immersion liquid or can be immersed at least with the front lens into the immersion liquid. Preferably the deflection means, for example one or more deflection mirrors, are also immersed into the immersion liquid during the investigation operation.

Provision can be made in particular that the sample holder comprises at least one strand-shaped sub-holder with which at least one sample, in particular a row of samples, is respectively retained. The advantage of such an embodiment is that during successive conveyance of the samples into the sample illumination position, the deflection means moves laterally along the sub-holder, and/or the strand-shaped sub-holder moves past the deflection means, for example a deflection mirror, in a linear motion. In particular, provision can advantageously also be made that during successive conveyance of the samples into the sample illumination position, the strand-shaped sub-holder is moved through between two deflection means, for example deflection mirrors, arranged opposite one another.

In a particular embodiment, the sample holder comprises multiple strand-shaped sub-holders with which at least one sample, in particular a row of samples, is respectively retained. Alternatively or additionally, provision can be made that the sample holder comprises multiple strand-shaped sub-holders that are oriented in a common plane and/or parallel to one another, and/or that the sample holder comprises multiple cube-shaped sub-holders with which at least one of the samples is respectively retained.

In another embodiment the sample holder comprises sub-holders embodied as dishes in which at least one sample is respectively arranged. Provision can also be made that the sample holder comprises an, in particular, cylindrical tube, in which at least one of the samples is held or in which several of the samples are arranged, in particular lined up. An embodiment of this kind also makes possible rapid and precise conveyance of the individual samples into the sample illumination position.

In a particular embodiment the sample illumination position is arranged outside the illumination objective but in the extended optical axis of the illumination objective. This makes possible precise, efficient, and space-saving illumination of at least one sample in each case. Such an arrangement moreover makes possible a particularly mechanically robust embodiment. The reason in particular is that long carrier arms for holding optical components, which can oscillate in disruptive fashion, are avoided. In particular, provision can be made here, advantageously, that the illumination light is guided eccentrically through the illumination objective.

In a particularly advantageous embodiment at least one sub-holder comprises a preferably transparent embedding medium, in particular agarose or a (preferably similar) gel-like transparent medium, and/or a similar gelatin-like transparent matrix, into which the sample or samples held by the sub-holder is or are embedded. An embodiment of this kind has the particular advantage that the respective sample can be observed with no shadowing by opaque holding components. In addition, an environment that is protective and favorable to preservation of the samples can be created by an embedding medium.

In a particular embodiment provision is made that the samples that have already been investigated and have already been removed from the sample illumination position are withdrawn, in particular automatically, from the sample holder. In particular, provision can additionally be made that further samples to be investigated are transferred, in particular automatically, to the sample holder, in particular to positions of the sample holder that have become vacant. This advantageously makes possible a continuous investigation process in which samples can be investigated successively, continuously, and without interruption.

As already mentioned, provision can be made, for example, that the sample holder is rotated in order to respectively position, in the illumination position, the next sample to be investigated. Provision can be made in particular that the sample holder is rotated around the optical axis of the illumination objective or around an axis parallel to the optical axis of the illumination objective in order to respectively position, in the illumination position, the next sample to be investigated. A procedure of this kind is advantageously appropriate in particular when the samples are arranged annularly in the sample holder.

Alternatively or additionally, provision can be made that the sample holder is displaced linearly relative to the illumination position in at least one direction in order to respectively position, in the illumination position, the next sample to be investigated; and/or that a displacement apparatus is present with which the sample holder is displaceable, in particular automatically, in two different, in particular mutually orthogonal, directions, and/or that a displacement apparatus is present with which the sample holder is displaceable, in particular automatically, in three different, in particular mutually orthogonal, directions.

In a particular embodiment the deflection means and the sample located in the illumination position are arranged in a common plane, the deflection means surrounding the sample located in the illumination position, within this plane, only incompletely, in particular only on one side or on two opposite sides. Preferably there remains exposed, within the aforesaid plane, at least one region through which samples can be conveyed into the sample illumination position and removed therefrom. An embodiment of this kind has the particular advantage that the samples can be stored with the sample holder in the aforesaid plane, and that a sample can respectively be conveyed into the sample illumination position or removed from it by way of one or more displacement motions of the samples exclusively in the aforesaid common plane, which in particular can also be the illumination plane, with no need for a positioning motion perpendicularly to the aforesaid common plane.

In a very particularly advantageous embodiment the type of sample holder respectively being used is recognized automatically, in particular in software-controlled fashion, so that the successive positioning of the samples in the sample illumination position can then be accomplished, in particular automatically, in consideration of the type that is recognized and/or using a position changing routine associated with the recognized type and, in particular, stored in a software memory. It is thereby possible to be able to use different types of sample holder, for example strand-shaped or turret-shaped sample holders, in which context the optical apparatus adapts, preferably automatically, to the current type at the time.

Advantageously, provision can be made that the samples to be investigated are arranged automatically, for example using an automatic loader, in the sample holder and/or in a sub-holder of the sample holder. Provision can furthermore advantageously be made here that the samples are advantageously oriented, preferably automatically, within the sample holder in terms of the microscopic investigation.

The light stripe can be generated, for example, with a cylindrical optic from a light bundle that is round in cross section, for example a laser. Alternatively, it is also possible for the light stripe to be a quasi-light stripe that is made up of a light bundle moved continuously back and forth in a light stripe plane. The optical apparatus can comprise for this purpose, for example, a beam deflection apparatus with which a light bundle is movable in an illumination plane preferably sufficiently rapidly that a light stripe exists de facto in the illumination plane; and/or that said illumination is not distinguishable, with the detectors provided for detection of the light emerging from the sample and with the downstream evaluation apparatuses of a microscope, from a continuous light stripe, for example one generated with a cylindrical optic; and/or that the acquired image data do not differ, or do not differ substantially, from the data that would be generated in the context of illumination with a continuous light stripe.

Preferably the light stripe plane in which the deflected light stripe propagates is oriented perpendicularly to the optical axis of the illumination objective and/or of the detection objective.

In a particular embodiment provision is made that the detected light emerging from the sample also proceeds through the illumination objective and/or is collimated with the illumination objective.

Alternatively, however, it is also possible for the detected light emerging from the sample to proceed through a detection objective and/or to be collimated with a detection objective. Provision can be made here in particular that the optical axis of the illumination objective and the optical axis of the detection objective are oriented in parallel fashion and/or collinearly with one another. An embodiment of this kind has the particular advantage that the optical apparatus can be embodied in particularly compact and robust fashion, and that the sample illumination region is particularly easily accessible, thus enabling rapid and precise successive conveyance of the samples into the sample illumination region.

Provision can in particular be made, advantageously, that the light stripe initially proceeds in a vertical direction through the illumination objective and is then deflected in a horizontal direction with the deflection means in order to illuminate a layer of the sample. The light, in particular fluorescent light, emerging from the illuminated layer preferably proceeds in a vertical direction through a detection objective. A configuration of this kind allows the use of standard upright or inverted microscope stands in order to produce the optical apparatus according to the present invention.

The deflection apparatus, which can comprise, for example, one or more deflection mirrors, can advantageously be mounted, in particular movably, on the illumination objective and/or on the detection objective. When an inverted microscope stand is used to produce the optical apparatus according to the present invention, a particularly robust and compact embodiment is made possible by the fact that the deflection means is held on the detection objective, which is arranged instead of a condenser at the condenser position of the inverted microscope stand.

In the interest of reliable adjustability of the irradiation direction and/or irradiation location on the respective sample located in the sample illumination position, provision can advantageously be made that the illumination objective and the deflection apparatus are arranged movably relative to one another, and/or that the deflection apparatus is mounted movably on the illumination objective, and/or that the deflection apparatus is mounted movably on the detection objective. An embodiment of this kind moreover advantageously allows an illumination objective having a high numerical aperture to be used even when a sample to be investigated is larger than the image field of the illumination objective. The usability of high-aperture illumination objectives has the particular advantage that the light stripe or quasi-light stripe that strikes the sample can be of particularly thin configuration, which increases resolution.

The fact that a movement of the detection objective preferably occurs only within defined regions will be discussed below.

The movement of the sample or sample holder in relation to the detection objective is restricted as a result of the respective lateral arrangement of the deflection means to the right and left. In order to avoid possible collisions with the sample, a safeguard is needed which permits positioning/movement of the sample stage or sample holder relative to the detection objective only within defined regions. These defined regions can be defined both via the control software and via mechanical and electronic switches.

To ensure that the deflection means does not collide with the sample, a sufficiently large clearance must be present between the sample and deflection means.

This clearance can also be used to position the site of interest within the sample at the center of the light stripe.

In particular in terms of the (preferably software-based) definition of the movement restriction, the predefined regions can be specified a) by the fact that the arrangement of multiple samples or sub-holders in a special sample chamber or on a special sample holder is or becomes accurately defined and is stored in the control software. This can be loaded as necessary, for example automatically by detection/readout upon the insertion of special sample holders, or manually. An exemplifying embodiment of a special sample holder is shown in FIG. 8; and/or b) by the fact that the samples or sub-holders contained in the sample holder are pre-investigated using an image-producing method, and the positions or arrangement of the samples/sub-holders are calculated by automatic image analysis of the acquired image. Various microscopy methods can be used for this, for example confocal, transmitted-light, phase-contrast, multi-photon, reflected, and epifluorescence microscopy. By using individual methods or a combination of several methods, it is thereby possible to identify those regions in which the sample stage can move without the occurrence of a collision between the deflection means and the sample. In addition, sample chambers and embedding media produced especially for this purpose can help characterize the sample space more accurately, for example thanks to the use of fluorescing markers.

A variety of optical methods can be used to detect the clearance or the definable region in which a relative motion between the deflection means and sample holder is possible without collision between the deflection means and sample. On the one hand it is conceivable to ascertain the transition from the coverslip or transparent base of the sample holder to the sample region, by confocal reflection measurement with illumination light through the illumination objective.

The reflection at the transition decreases if a sample is placed on the coverslip, since typically the refractive index of the sample is higher than that of the aqueous medium. The greater the difference in refractive index between the coverslip and the medium/sample, the greater the reflection at the transition as well. It is thereby possible to identify where the sample is placed, and thus the clearance between adjacent sample regions.

Methods that utilize the absorption of the sample are a further possibility for identifying the clearance. Using both wide field light-microscopy methods and scanning light-microscopy methods, it is possible to acquire images that depict the outlines of the sample and thus the clearance between the various samples.

If the absorption behavior of the sample is low, further contrast-enhancing methods, for example differential interference contrast (DIC) or phase contrast, can be used to better depict the outlines.

It is also conceivable to add a dye at least in part to a sample support medium (e.g. agar, hydrogel) so that that support, or the embedding medium, can be detected. This dye can both absorb and fluoresce. This dye, and thus the sample region, can be identified using both wide field microscopy or confocal/multi-photon microscopy.

Very generally, and in particular also independently of the present invention, a sample holder could also be embodied as follows:

The sample holder encompasses a sufficiently dimensioned safe region (safety border) that is dimensioned in such a way that a detection objective having deflection means is movable around a restricted motion region. No "obstacles," in the form of samples and/or sub-holder(s) that can cause a collision with the detection objective or the deflection means, are present in this safety border. In addition, the sample holder could comprise a restricted motion region in which individual samples or sub-holders can be arranged. Preferably these arbitrarily arranged samples or sub-holders each have a definable or necessary spacing with respect to the adjacent samples or sub-holders, in order to enable scanning or imaging of the samples without destruction of a sample by the detection objective or deflection means.

Scanning of the sample or sub-holders in only one direction is possible in particular when the samples or sub-holders are arranged in substantially parallel fashion and with a suitable spacing. The suitable spacing depends on the dimensioning of the deflection means.

The sample holder preferably comprises markings that can be arranged, in particular, in the restricted motion region. Correct placement of samples on the sample holder can thereby be facilitated for an operator, so that the necessary spacings between adjacent sub-holders or sample rows can be complied with.

BRIEF DESCRIPTION OF THE DRAWING VIEWS

The subject matter of the invention is schematically depicted in the drawings and will be described below with reference to the Figures, identically functioning elements being labeled with the same reference characters. In the drawings.

Figure 7:
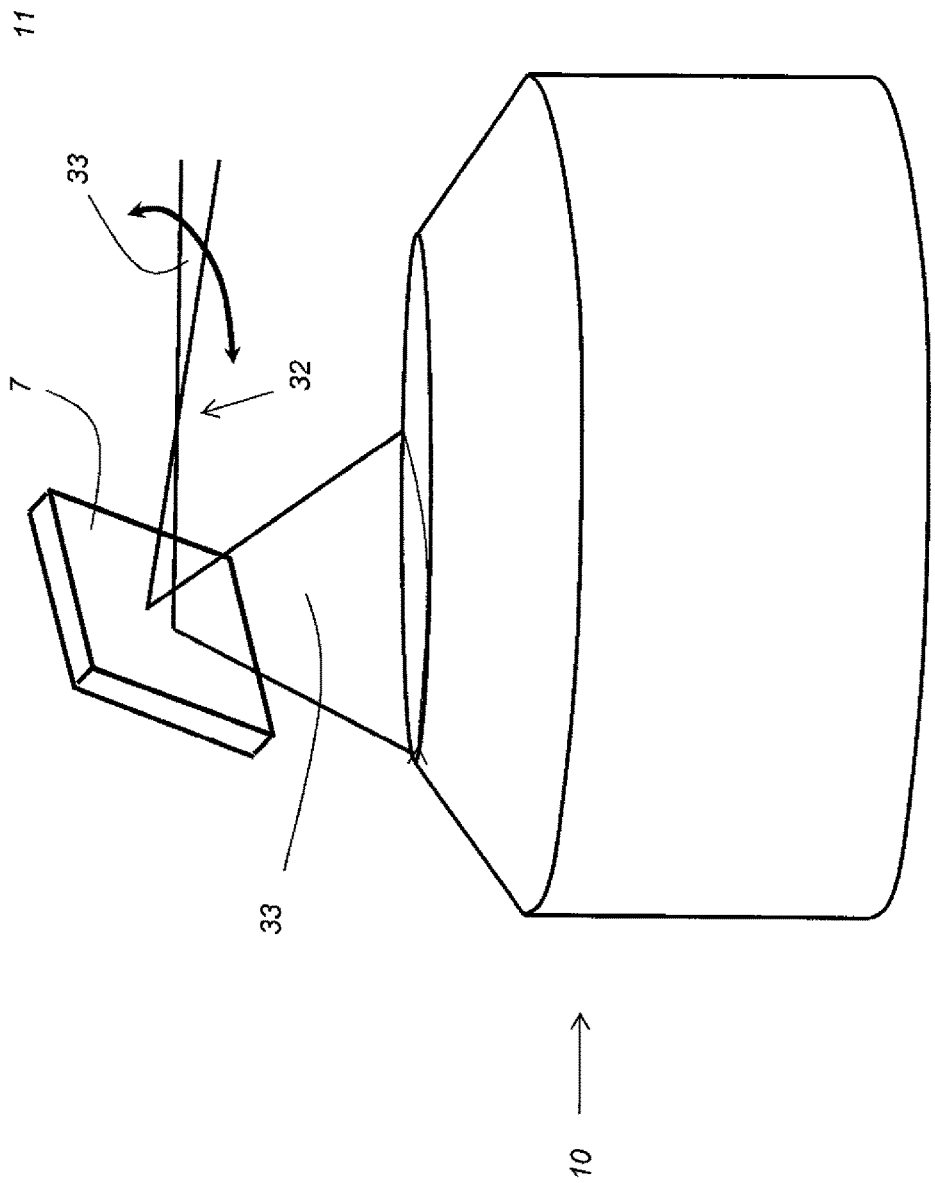
Figure 8:
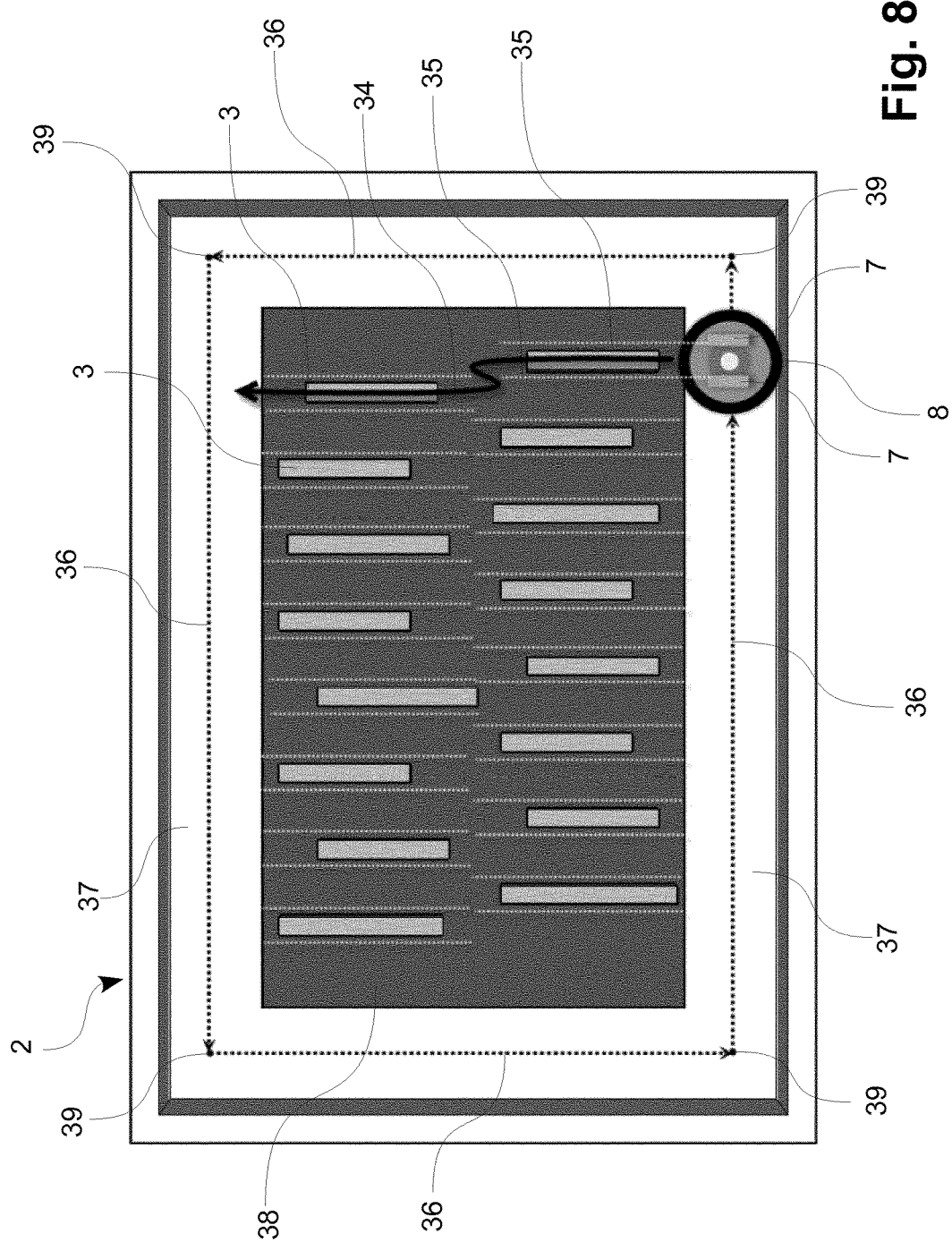
Figure 9:
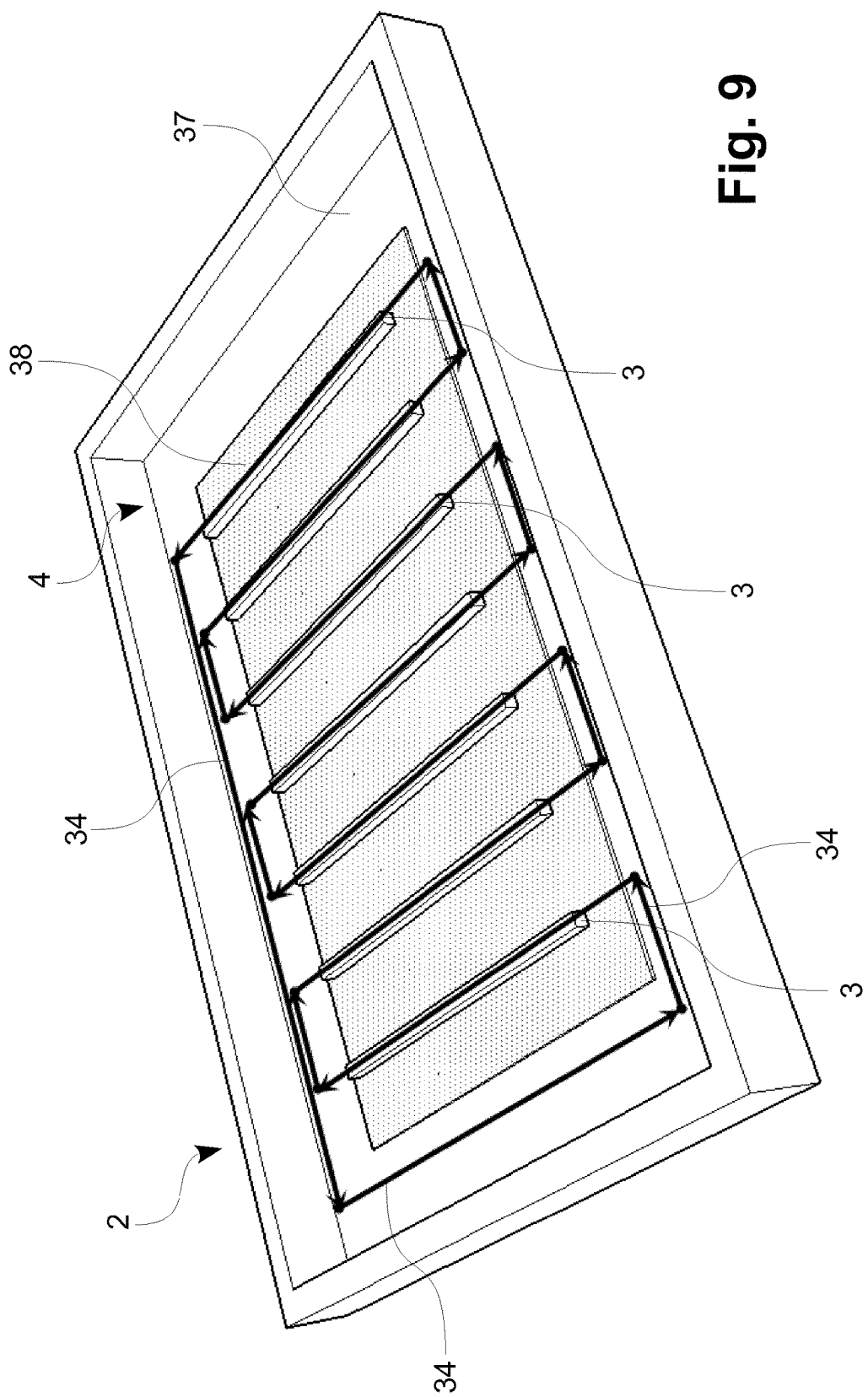
Figure 10:
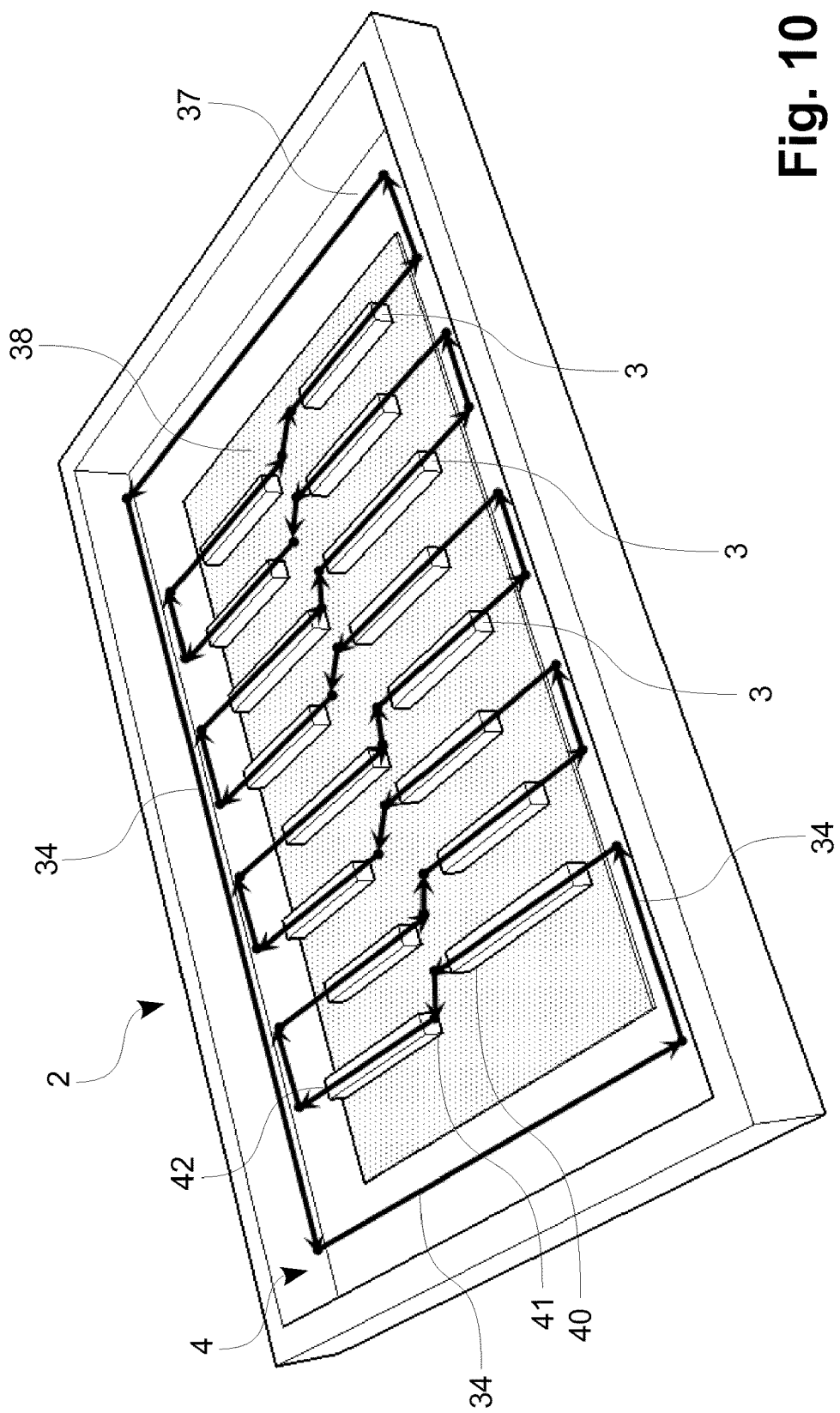

FIG. 7 schematically depicts a possible path of the light stripe;

FIG. 8 is a plan view showing an exemplifying embodiment of a special sample holder;

FIG. 9 is a perspective view of an exemplifying embodiment of a sample holder having sub-holders; and FIG. 10 is a perspective view of a further exemplifying embodiment of a sample holder having sub-holders.

DETAILED DESCRIPTION OF THE INVENTION

Figure 1:
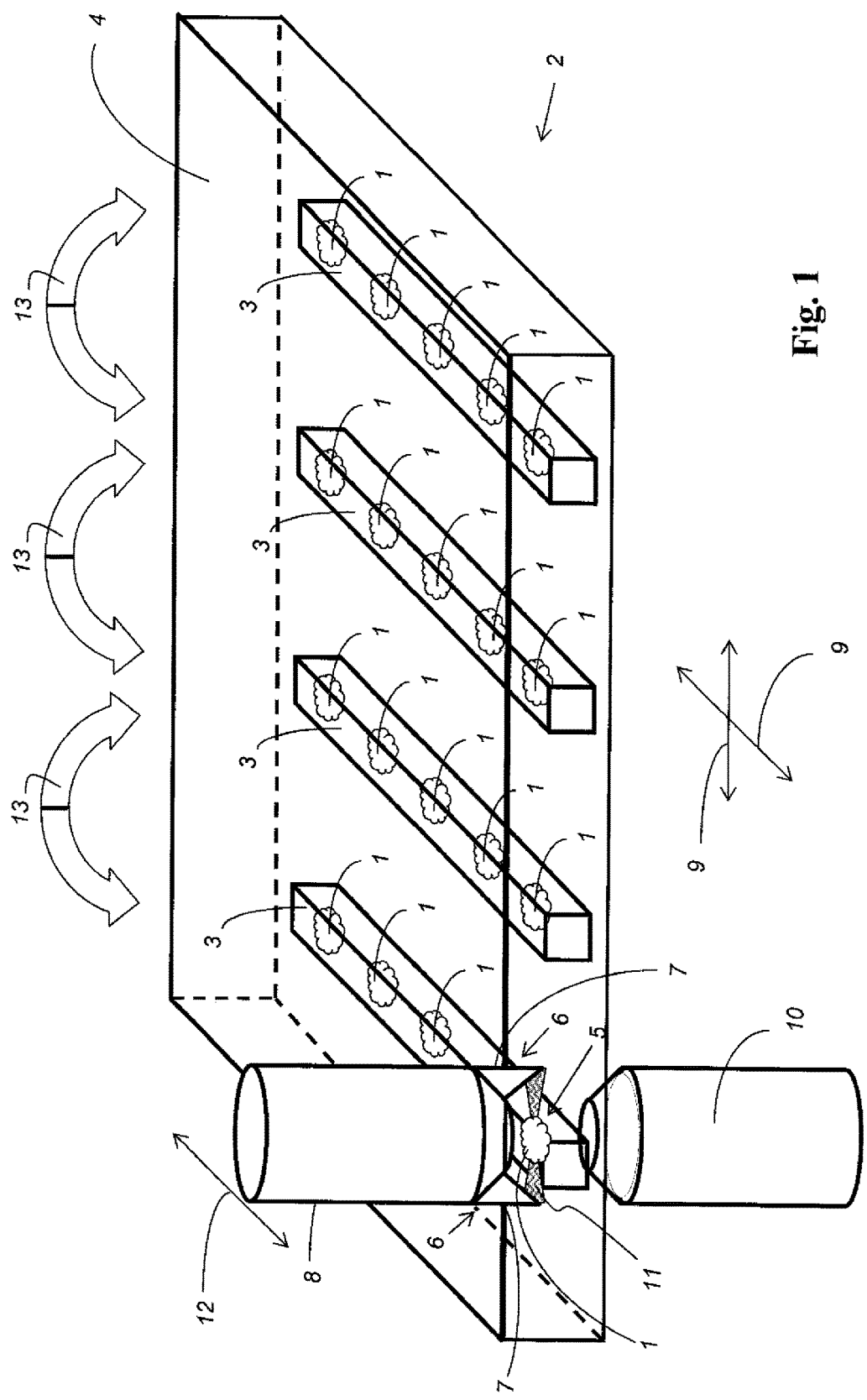
FIG. 1 is a detail view of an exemplifying embodiment of an optical apparatus according to the present invention, to explain a possible embodiment of the method according to the present invention.

FIG. 1 is a detail view of an exemplifying embodiment of an optical apparatus according to the present invention for microscopic investigation of a plurality of samples 1, to explain a possible embodiment of the method according to the present invention.

The optical apparatus comprises a sample holder 2, samples 1 to be investigated being retained in multiple sub-holders 3 of sample holder 2. Sub-holders 3 are each embodied as a strand-shaped cuboid. Each sub-holder 3 is made up of a dimensionally stable embedding medium, for example agarose, or of a (preferably similar) gel-like transparent medium, into which samples 1 held by the respective sub-holder 3 are embedded. Sub-holders 3 are arranged in a common, preferably horizontal plane, and parallel to one another, in a transparent dish 4 of sample holder 2, which dish is filled with an immersion liquid (not depicted). As a result of this special embodiment of sample holder 2 and the special arrangement of samples 1 that are held, there advantageously remains on both sides of samples 1 a respective clearance for a deflection means 6 that comprises two deflection mirrors 7 held by a detection objective 8.

Detection objective 8 is immersed into the immersion liquid (not depicted) during the microscopic investigation of one of the samples. Deflection means 6, which is attached to detection objective 8, is located in the immersion liquid during the microscopic investigation.

Deflection means 6 serves to deflect a light stripe 11, which has emerged from an illumination objective 10, to an illumination position 5 in such a way that light stripe 11 propagates at an angle different from zero degrees, in particular at a right angle, with respect to the optical axis of illumination objective 10. In this manner, a layer of sample 1 that is located in illumination position 5 is illuminated by the light stripe focused by illumination objective 10.

For the sake of better clarity, light stripe 11 is depicted only partly and schematically in FIG. 1 and in FIGS. 2 to 6. FIG. 7 contains a somewhat more accurate depiction of the path of light stripe 11.

The detected light, in particular fluorescent light, emerging from the illuminated layer is directed through detection objective 8 to a detector (not depicted in FIG. 1). The detector can comprise, for example, a sensor for acquiring a two-dimensional image, for example a CCD sensor.

Once the desired image information regarding the illuminated layer has been acquired, sample holder 2 and sample 1 that is respectively located in sample illumination position 5 can be displaced relative to one another, perpendicularly to the plane of the deflected light stripe 11 and/or parallel to the optical axis of illumination objective 10, in order to illuminate and microscopically investigate a further, different layer of sample 1. Alternatively, it is also possible to move the deflection means and/or illumination objective 10 in order to illuminate a different layer of sample 1 with the deflected light stripe 11. For example, illumination objective 10 can be moved in the direction of its optical axis in order to change the illuminated layer. Alternatively or additionally it is also possible, for example, to displace deflection means 6 parallel to the plane of the deflected light stripe 11 and/or perpendicularly to the optical axis of illumination objective 10 in order to illuminate a different layer of sample 1 with the deflected light stripe 11.

By successive scanning of multiple layers it is thus possible to obtain a three-dimensional image of the respective sample 1 present in sample illumination position 5, or to obtain image data that make possible a three-dimensional image of the respective sample 1 located in sample illumination position 5.

Sample holder 2, which holds samples 1, is preferably supported movably, preferably in motorized and/or automatic fashion, relative to sample illumination position 5 in such a way that at least one of samples 1 is respectively successively positionable in sample illumination position 5. Sample holder 2 is preferably arranged to be guidedly movable with a displacement apparatus in two mutually perpendicular directions, one of which is preferably the longitudinal extension direction of sub-holder 3; this is illustrated in the Figure by double arrows 9.

Because sufficient clearance for deflection means 6 remains laterally alongside and between sub-holders 3, the next sample can be respectively conveyed into illumination position 5, and microscopically investigated, by means of a simple, in particular horizontal, linear motion of sample holder 2 relative to illumination objective 10. Advantageously, switching from one sample 1 to the next sample 1 of the same sub-holder 3 merely and exclusively requires a single linear motion of sample holder 2 relative to illumination objective 10, which is indicated by double arrow 12. A relative motion of the detection objective, together with the deflection means, additionally in a vertical direction is required only in order to switch from one sub-holder 3 to the next sub-holder 3, as illustrated by the curved double arrows 13.

Figure 2:
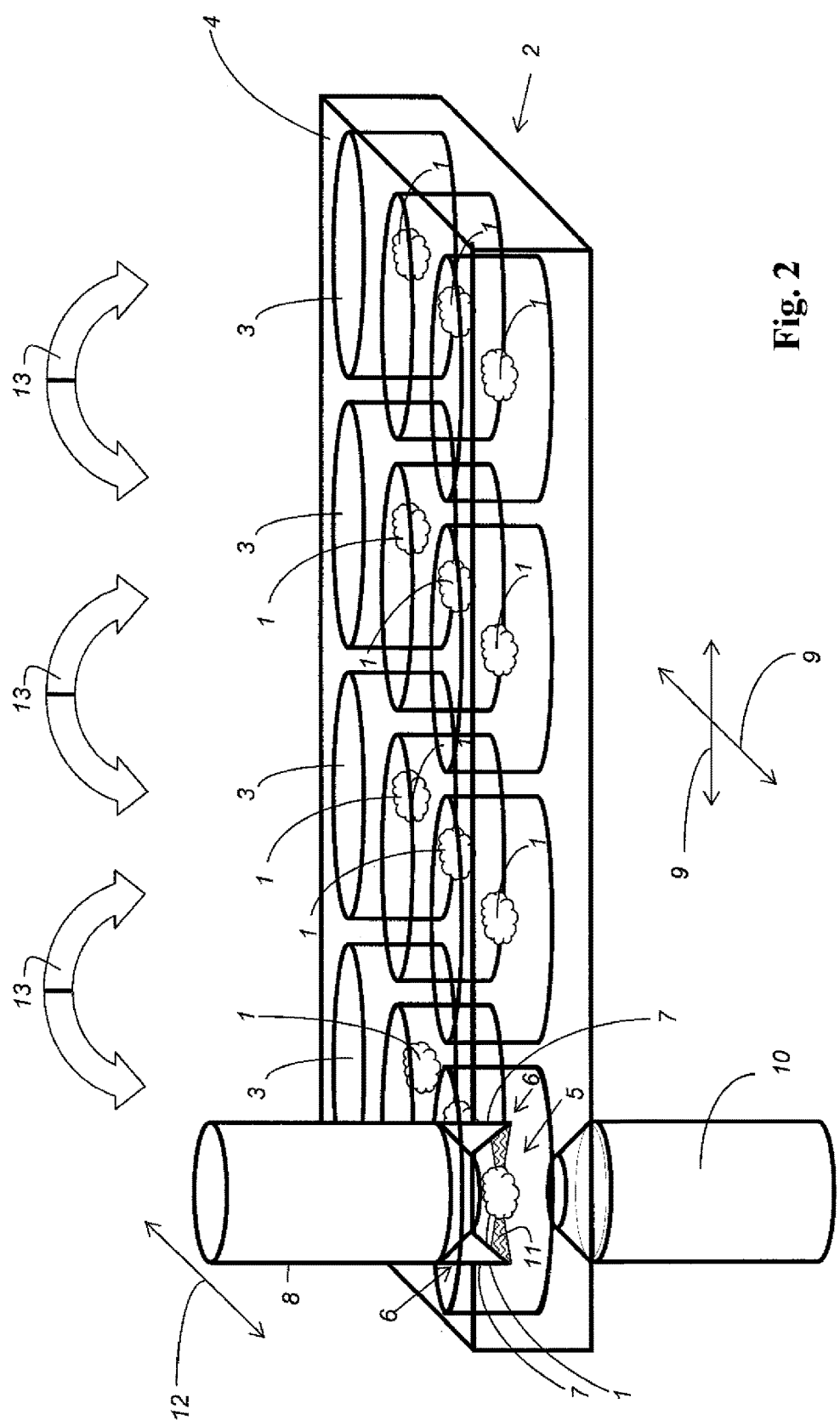
FIG. 2 is a detail view of another exemplifying embodiment of an optical apparatus according to the present invention, to explain another possible embodiment of the method according to the present invention.

FIG. 2 is a detail view of another exemplifying embodiment of an optical apparatus according to the present invention. In this embodiment sub-holders 3 of sample holder 2 are arranged in a transparent dish 4, as in the embodiment shown in FIG. 1. Unlike in the embodiment shown in FIG. 1, however, sub-holders 3 of the sample holder are embodied as further dishes, transparent and filled with a transparent, preferably liquid, embedding medium, in each of which at least one sample 1 is arranged. The further dishes are arranged within transparent dish 4 in matrix form in one common plane.

In order to position a sample 1 in illumination position 5, detection objective 8 together with the deflection means is respectively introduced from above into the further dishes; this is illustrated in the Figure by the curved double arrows 13. In this embodiment as well, the sample holder is arranged to be guidedly movable with a displacement apparatus (not depicted) in two mutually perpendicular directions; this is illustrated in the Figure by double arrows 9.

Figure 3:
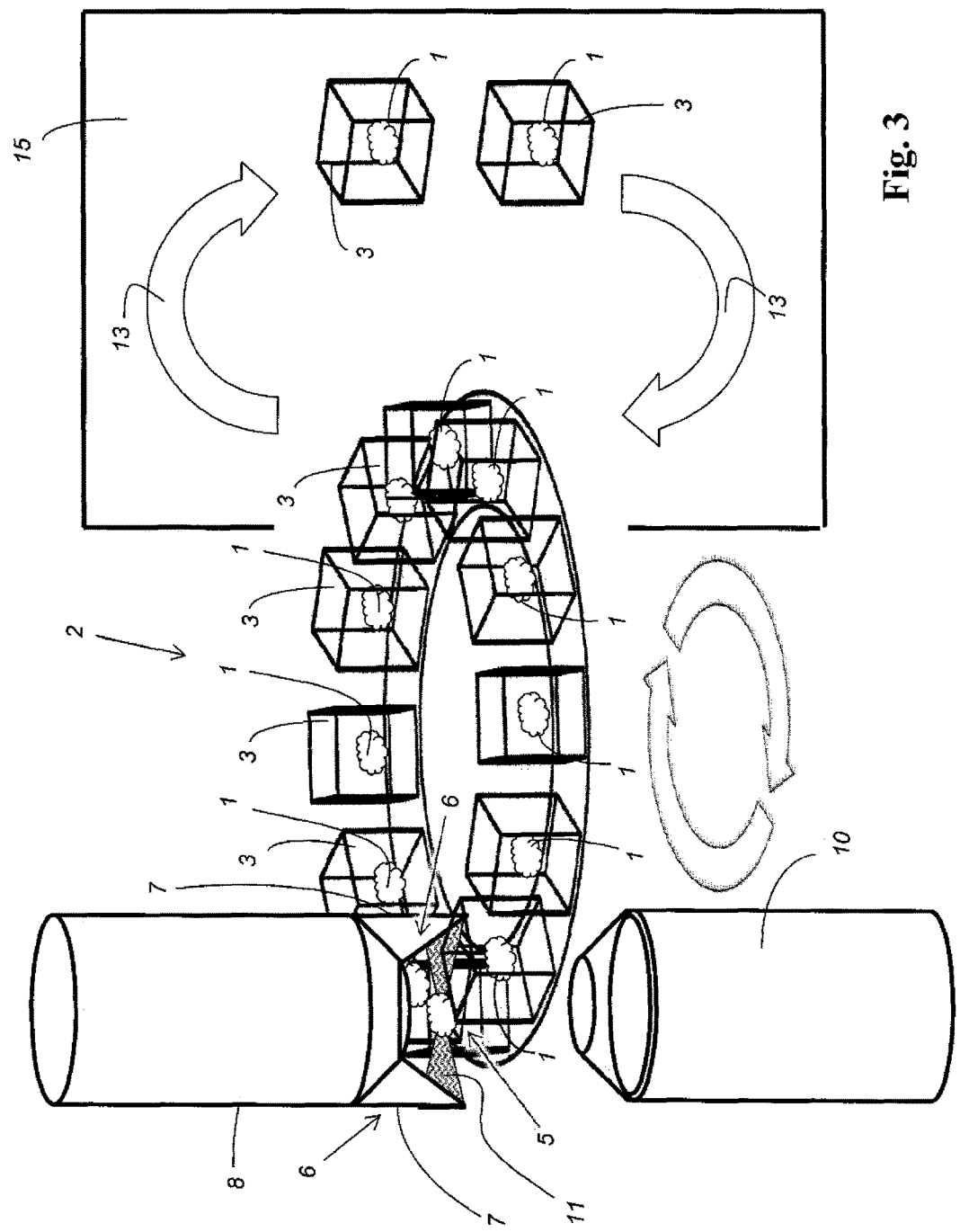
FIG. 3 is a detail view of a further exemplifying embodiment of an optical apparatus according to the present invention, to explain a further possible embodiment of the method according to the present invention.

FIG. 3 is a detail view of a further exemplifying embodiment of an optical apparatus according to the present invention, in which sample holder 2 comprises a revolving turret 14 that carries a plurality of samples 1 each held in a sub-holder 3. Sub-holders 3 are of cube-shaped configuration, but there is no limitation to such a shape; other geometric shapes are instead also possible. Sub-holders 3 are each made of a dimensionally stable embedding medium, for example agarose or a (preferably similar) gel-like, transparent medium into which at least one sample 1 is respectively embedded.

The samples can be successively conveyed into illumination position 5, and microscopically investigated, by a rotation of turret 14.

The exemplifying embodiment shown in FIG. 3 furthermore comprises a handling apparatus that automatically arranges sub-holders 3, having samples 1 to be investigated, in turret 14, and withdraws samples 1 already investigated, together with their sub-holders 3, from turret 14.

Provision can be made here in particularly advantageous fashion that handling apparatus 14 preferably automatically withdraws samples 1 that have already been investigated, and have already been removed from sample illumination position 5 by a rotation of turret 14, from turret 14, and transfers further samples 1 yet to be investigated, together with their sub-holders 3, to turret 14, in particular to the positions that have become vacant due to the withdrawal of samples 1 that have already been investigated. What is advantageously achieved in this manner is a continuous investigation process in which samples 1 can be investigated successively, continuously, and uninterruptedly.

For the sake of better clarity, as already mentioned, light stripe 11 is depicted only partly and schematically in FIG. 3. In addition, for the sake of better clarity, in the illumination region some contour lines of sub-holder 3 therein are not depicted, or are depicted only partly.

Figure 4:
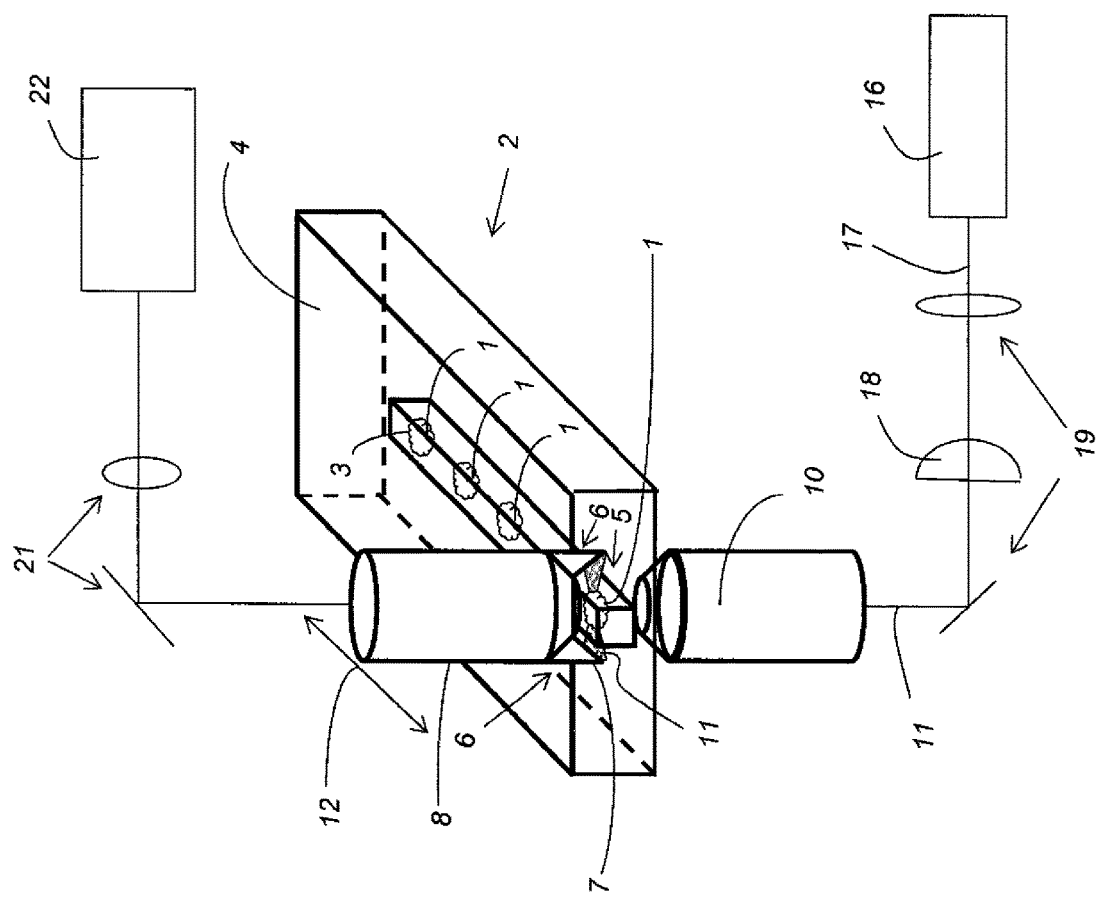
FIG. 4 shows an exemplifying embodiment of a possible optical apparatus according to the present invention.

FIG. 4 shows an exemplifying embodiment of a possible optical apparatus according to the present invention, having a sample carrier 2 that is configured similarly to the sample carrier shown in FIG. 1. Sample carrier 2 contains, however, only one sub-carrier 3.

The optical apparatus comprises a light source 16, which is embodied as a laser and emits a light bundle 17 that is substantially round in cross section. Light bundle 17 is shaped with the aid of a cylindrical optic 18 into a light stripe 11, and then travels to illumination objective 10. Optical elements 19, for example mirrors and lenses, are present in order to guide and shape light bundle 17 and light stripe 11. The illumination operation proceeds as described above with reference to the embodiment depicted in FIG. 1.

Detected light 20 emerging from sample 1 travels via further optical elements 21 to a detector 22.

Figure 5:
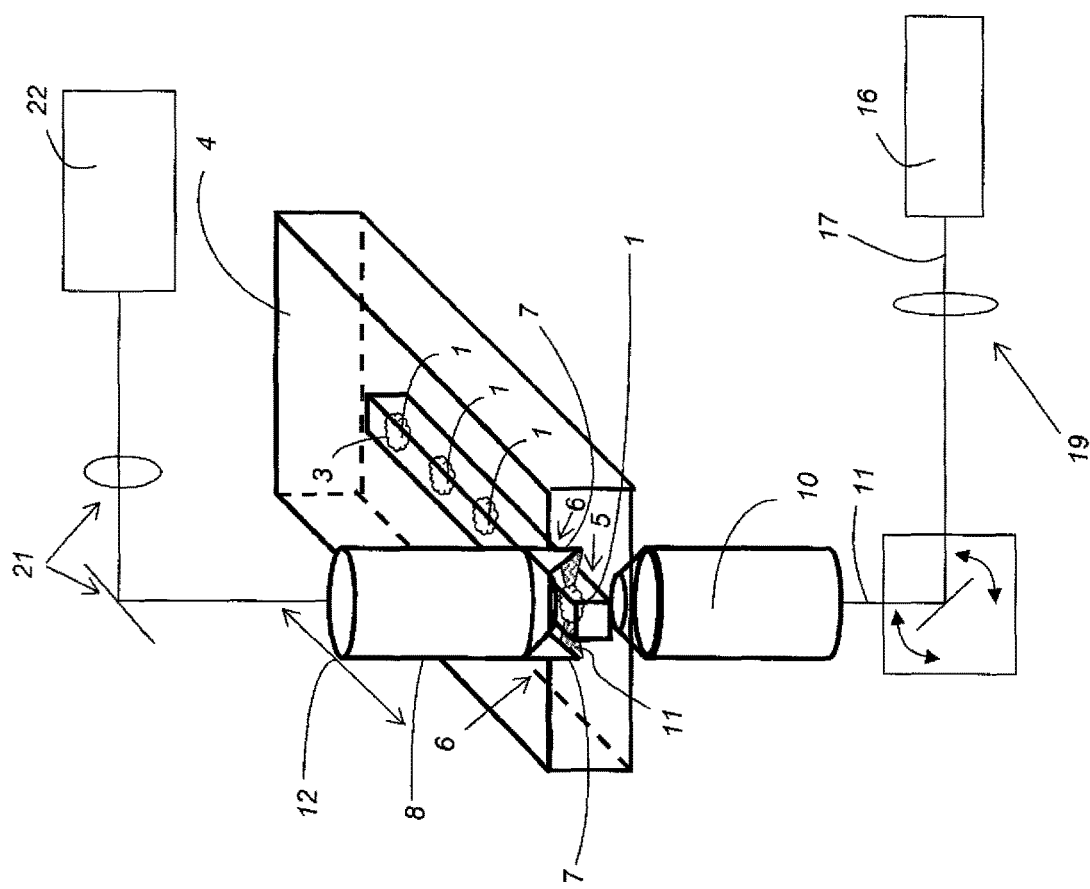
FIG. 5 shows an exemplifying embodiment of a modified optical apparatus according to the present invention.

FIG. 5 shows an exemplifying embodiment of an embodiment modified with respect to the embodiment depicted in FIG. 4. In this embodiment light bundle 17, round in cross section, that is generated by light source 16 is deflected in a plane with the aid of a beam deflection device 23, which for example can contain a galvanometer mirror, sufficiently rapidly that a light stripe 11 exists de facto in the illumination plane; and/or that said illumination is not distinguishable, with detectors 22 provided for detection of the light emerging from sample 1 and with the downstream evaluation apparatuses of a microscope, from a light stripe 11 generated with a cylindrical optic; and/or that the acquired image data do not differ, or do not differ substantially, from the data that would be generated in the context of illumination with a continuous light stripe 11.

Figure 6:
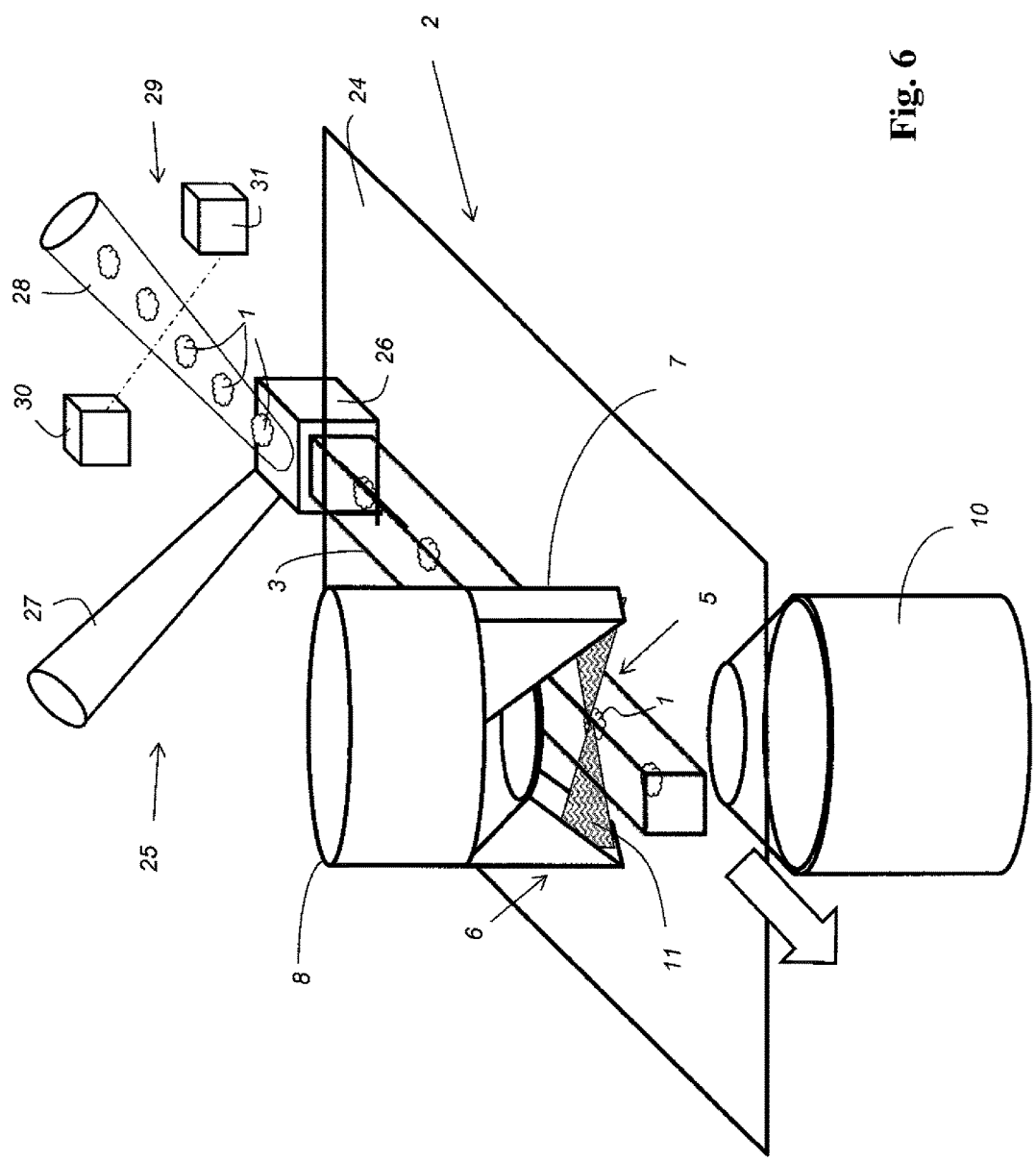
FIG. 6 shows another exemplifying embodiment of a possible optical apparatus according to the present invention.

FIG. 6 shows another exemplifying embodiment of a possible optical apparatus according to the present invention.

In this exemplifying embodiment sample holder 2 is made up of a transparent specimen carrier plate 24 that carries a cuboidal sub-holder 3 made of agarose or of a similar medium. Samples 1 to be investigated are embedded into the cuboids. In order to sequentially convey the individual samples 1 to be investigated into illumination position 5, sample holder 2 is moved stepwise in the longitudinal extension direction of sub-holder 3.

One special feature is the fact that sub-holder 3 is produced in the course of the investigation process. A sub-holder generating means 25, which comprises a molding means 26, is present for this. Sub-holder generating means 25 receives on the one hand, via a first feed conduit 27, agarose or a similar transparent medium, and on the other hand, via a second feed conduit 28, samples 1 to be embedded. Also provided is a light barrier arrangement 29 having a light source 30 and a light receiver 31, which detects the succession of samples 1 delivered through second feed conduit 28.

Molding means 26 is arranged in stationary fashion relative to illumination objective 10, and does not move along with specimen carrier plate 24.

FIG. 7 schematically depicts a possible path of light stripe 11. In this exemplifying embodiment light stripe 11 is generated by the fact that a light bundle 33 is moved continuously back and forth with a beam deflection device (not depicted); this is indicated in the Figure by the curved double arrow. For the sake of better clarity, the Figure depicts for this purpose only a brief "snapshot."

Light bundle 33, which emerges from illumination objective 10, is moved continuously back and forth and is focused by illumination objective 10, travels to a deflection mirror 7, and is deflected by the latter in such a way that it then propagates at an angle different from 0°, in the present example at an angle of 90°, with respect to the optical axis of illumination objective 10. Light bundle 33 has a focus 32 in illumination position 5. The quasi-light stripe 11 generated by the rapid back-and-forth motion is consequently located in a plane perpendicular to the optical axis of illumination objective 10.

It is also possible, but not obligatorily necessary, to illuminate sample 1 respectively located in illumination position 5 from different directions (simultaneously or sequentially) using multiple light stripes 11 that, after deflection, preferably all propagate in the same illumination plane. For the sake of better clarity, however, this instance is not depicted in the Figure.

FIG. 8 shows an exemplifying embodiment of a special sample holder. The reference number 34 indicates the motion direction of detection objective 8 (which is indicated only schematically) for which a collision does not occur between deflection means 6 or deflection mirrors 7 and the sample strip or sub-holder 3. A sample strip can be constituted, for example, from agar-agar, and can contain one to several samples. Dotted lines 35 that are drawn in indicate the motion path of deflection mirrors 7; deflection mirrors 7 can be moved in the clearance or definable region without colliding with the sample strip or sub-holder 3. In principle, the clearance or definable region depends on the spacing of the two deflection mirrors 7 and on the dimension of the sample strip or sub-holder 3. In addition, the spacing between two adjacent sub-holders 3 must be sufficient to avoid collisions between sub-holders 3 and deflection means 6 or deflection mirrors 7, or other components that are arranged on detection objective 8.

Center dotted line 36 shows a possible motion path in a safe region 37 in which detection objective 8 can move without intersecting a sample strip or sub-holder 3. Restricted motion region 38 in which the sample strips or sub-holder 3 are allowed to be located is shown with a gray background. In restricted motion region 38, a relative motion between sample holder 2 and detection objective 8 is allowed to occur only in specific motion tracks parallel to sub-holder 3, specifically so as to ensure always that a sample or sub-holder 3 cannot be damaged by observation objective 8. Sample holder 2 comprises integrated calibration objects or markers 39 that comprise salient points at defined positions, fluorescing dots, fluorescing patterns (bead cluster), or microstructures visible in the microscopic transmitted-light mode. An integrated marker 39 of this kind could also, in particular, serve calibration purposes: it could be traveled to in order to allow, for example, determination of a relative position between the illumination objective and/or detection objective and sample holder 2.

FIG. 9 is a perspective view showing an exemplifying embodiment of a sample holder 2 having sub-holders 3 of substantially elongated configuration in a dish 4. Sub-holders 3 are arranged substantially parallel to one another. Motion track 37 of the detection objective (not shown in FIG. 9) has a meander shape, or extends in the safe region along the longitudinal side and transverse side of sample holder 2. With a special sample holder 2, the positions of sub-holders 3 can be predefined. The positions can be read out from a memory when the system recognizes that samples are to be detected on the special sample holder 2.

FIG. 10 is a perspective view showing a further exemplifying embodiment of a sample holder 2 having sub-holders 3 in a dish 4. Sub-holders 3 can have different lengths, and are arranged substantially parallel to one another. The longitudinal directions of sub-holders 3 can, however, also be oriented in other directions (not shown), or can be arranged not in parallel fashion. FIG. 10 shows a motion path 37, calculated in optimized fashion, of the detection objective (not shown in FIG. 10). This could be the shortest motion path of the detection objective and/or the shortest detection time span, while a collision between the detection objective/deflection means and the sample is nevertheless to be avoided. For example, within restricted motion region 38 the shortest motion path between end point 40 of the one sub-holder 3 and starting point 41 of the next sub-holder 3 is ascertained. If end point 42 is located close to the edge of restricted motion region 38, the next sub-holder 3 is traveled to via safe region 37.

What is claimed is:

1. A method for microscopic investigation of a plurality of samples, characterized by the following steps:
   a. arranging the samples in a sample holder that is movable or is movable in a motorized or automatic fashion, relative to a sample illumination position in such a way that at least one of the samples is respectively successively positionable in the sample illumination position, a clearance for a deflection means respectively remaining adjacent to the sample that is currently located in the sample illumination position;
   b. focusing a light stripe with an illumination objective;
   c. deflecting the light stripe, once it has passed through the illumination objective, with the deflection means in such a way that the light stripe propagates at an angle different from zero degrees or at an angle greater than 10 degrees or at a right angle, with respect to the optical axis of the illumination objective, and has a focus in the sample illumination position; and
   d. successively positioning the samples, retained with the sample holder, in the sample illumination position, and detecting a detected light emerging from the sample respectively located in the sample illumination position, wherein
   e. the samples are held with the sample holder in at least one straight row; or
   f. the samples are held with the sample holder in a curved row or in an annular row;
   and wherein
   g. a displacement apparatus is present with which the sample holder is displaceable in three different directions or in mutually orthogonal directions;
   wherein the type of sample holder respectively being used is recognized automatically or in a software-controlled fashion; and the successive positioning of the samples in the illumination position is accomplished in consideration of the type that is recognized and/or using a position changing routine associated with the recognized type and/or stored in a software memory.

2. The method according to claim 1, wherein
   a. one or more of the samples are retained in a sub-holder of the sample holder; or
   b. the sample holder comprises multiple sub-holders with which at least one sample is respectively retained; or
   c. the sample holder comprises at least one strand-shaped sub-holder with which at least one sample or a row of samples, is respectively retained; or
   d. the sample holder comprises multiple strand-shaped sub-holders that are oriented in a common plane and/or parallel to one another; or
   e. the sample holder comprises multiple cube-shaped sub-holders with which at least one of the samples is respectively retained; or
   f. the sample holder comprises sub-holders embodied as dishes in which at least one sample is respectively arranged; or
   g. the sample holder comprises a tube, in which at least one of the samples is held or in which several of the samples are arranged or lined up; or
   h. the sample illumination position is arranged outside the illumination objective but in the extended optical axis of the illumination objective.

3. The method according to claim 2, wherein at least one sub-holder comprises an embedding medium or an agarose or a gel-like transparent medium, into which the sample or samples held by the sub-holder is or are embedded.

4. The method according to claim 1, wherein
   a. the samples that have already been investigated and have already been removed from the sample illumination position are withdrawn from the sample holder; or
   b. the samples that have already been investigated and have already been removed from the sample illumination position are withdrawn from the sample holder, and further samples to be investigated are transferred to the sample holder or to positions of the sample holder that have become vacant.

5. The method according to claim 1, wherein
   a. the sample holder is rotated in order to respectively position, in the illumination position, the next sample to be investigated; or b. the sample holder is rotated around the optical axis of the illumination objective or around an axis parallel to the optical axis of the illumination objective in order to respectively position, in the illumination position, the next sample to be investigated; or c. the sample holder is displaced linearly relative to the illumination position in at least one direction in order to respectively position, in the illumination position, the next sample to be investigated; or d. a displacement apparatus is present with which the sample holder is displaceable in two different directions or in mutually orthogonal directions.

6. The method according to claim 1, wherein
a. the deflection means and the sample located in the illumination position are arranged in a common plane, the deflection means surrounding the sample located in the illumination position, within this plane, only incompletely or only on one side or on two opposite sides; or
b. there remains exposed, within a plane in which the sample illumination position and the deflection means are located, at least one region through which samples can be conveyed into the sample illumination position and removed therefrom.

7. The method according to claim 1, wherein the samples to be investigated are arranged automatically in the sample holder and/or in a sub-holder of the sample holder.

8. The method according to claim 1, wherein the light stripe is a quasi-light stripe that is made up of a light bundle moved continuously back and forth in a light stripe plane.

9. The method according to claim 1, wherein the light stripe is coupled into the illumination objective in such a way that it proceeds eccentrically through the illumination objective.

10. The method according to claim 1, wherein the detected light emerging from the sample also proceeds through the illumination objective and/or is collimated with the illumination objective.

11. The method according to claim 1, wherein the detected light emerging from the sample proceeds through a detection objective and/or is collimated with a detection objective.

12. The method according to claim 11, wherein the optical axis of the illumination objective and the optical axis of the detection objective are oriented in parallel fashion and/or collinearly with one another.

13. The method according to claim 1, wherein
a. the illumination objective and a deflection apparatus are arranged movably relative to one another; or
b. a deflection apparatus is mounted movably on the illumination objective; or
c. a deflection apparatus is mounted movably on the detection objective.

14. An optical apparatus having a sample holder that holds a plurality of samples and is supported movably or is movable in a motorized and/or automatic fashion, relative to a sample illumination position in such a way that at least one of the samples is respectively successively positionable in the sample illumination position, wherein a clearance for a deflection means is present respectively adjacent to the sample that is currently located in the sample illumination position, said means deflecting the light stripe emerging from an illumination objective to the illumination position in such a way that the light stripe propagates at an angle different from zero degrees or at a right angle, with respect to the optical axis of the illumination objective; and having a detector that detects the detected light emerging from the sample respectively located in the sample illumination position, wherein
a. the samples are held with the sample holder in at least one straight row; or
b. the samples are held with the sample holder in a curved row or in an annular row;
and wherein
c. a displacement apparatus is present with which the sample holder is displaceable in three different directions or in mutually orthogonal directions;
wherein
d. a control apparatus is present which rotates the rotatably supported sample holder in order to respectively position, in the illumination position, the next sample to be investigated; or
e. a control apparatus is present which rotates the sample holder around the optical axis of the illumination objective or around an axis parallel to the optical axis of the illumination objective in order to respectively position, in the illumination position, the next sample to be investigated; or
f. a control apparatus is present which, with a displacement apparatus, linearly displaces the displaceably supported sample holder relative to the illumination position in at least one direction in order to respectively position, in the illumination position, the next sample to be investigated; or
g. a displacement apparatus is present with which the sample holder is displaceable in two different directions or in mutually orthogonal directions.

15. The optical apparatus according to claim 14, wherein
a. one or more of the samples are retained in a sub-holder of the sample holder; or
b. the sample holder comprises multiple sub-holders with which at least one sample is respectively retained; or
c. the sample holder comprises at least one strand-shaped sub-holder with which at least one sample or a row of samples, is respectively retained; or
d. the sample holder comprises multiple strand-shaped sub-holders that are oriented in a common plane and/or parallel to one another; or
e. the sample holder comprises multiple cube-shaped sub-holders with which at least one of the samples is respectively retained; or
f. the sample holder comprises sub-holders embodied as dishes in which at least one sample is respectively arranged; or
g. the sample holder comprises a tube, in which at least one of the samples is held or in which several of the samples are arranged or lined up; or
h. the sample illumination position is arranged outside the illumination objective but in the extended optical axis of the illumination objective.

16. The optical apparatus according to claim 15, wherein at least one sub-holder comprises an embedding medium or agarose or a gel-like transparent medium, into which the sample or samples held by the sub-holder is or are embedded.

17. The optical apparatus according to claim 14, wherein a handling apparatus is present which
a. withdraws from the sample holder the samples that have already been investigated and have already been removed from the sample illumination position; or
b. withdraws from the sample holder the samples that have already been investigated and have already been removed from the sample illumination position, and transfers to the sample holder or to positions of the sample holder that have become vacant, further samples to be investigated.

18. The optical apparatus according to claim 14, wherein
   a. the deflection means and the sample located in the illumination position are arranged in a common plane, the deflection means surrounding the sample located in the illumination position, within this plane, only incompletely or only on one side or on two opposite sides; or
   b. there remains exposed, within a plane in which the sample illumination position and the deflection means are located, at least one region through which samples can be conveyed into the sample illumination position and removed therefrom.

19. The optical apparatus according to claim 14, wherein a control apparatus automatically recognizes or in a software-controlled fashion the type of sample holder respectively being used, and performs the successive positioning of the samples in the sample illumination position in consideration of the type that is recognized and/or using a position changing routine associated with the recognized type and/or stored in a software memory.

20. The optical apparatus according to claim 14, wherein a handling apparatus is present which automatically arranges, in the sample holder or in a sub-holder of the sample holder, the samples to be investigated, or removes from the sample holder samples that have already been investigated.

21. The optical apparatus according to claim 14, wherein the light stripe is a quasi-light stripe that is made up of a light bundle moved continuously back and forth, with a beam deflection device, in a light stripe plane.

22. The optical apparatus according to claim 14, wherein the light stripe proceeds eccentrically through the illumination objective.

23. The optical apparatus according to claim 14, wherein the detected light emerging from the sample proceeds through the illumination objective and/or is collimated by the illumination objective.

24. The optical apparatus according to claim 14, wherein the detected light emerging from the sample proceeds through a detection objective and/or is collimated by a detection objective.

25. The optical apparatus according to claim 24, wherein the optical axis of the illumination objective and the optical axis of the detection objective are oriented in parallel fashion and/or collinearly with one another.

26. The optical apparatus according to claim 14, wherein
   a. the illumination objective and a deflection apparatus are arranged movably relative to one another; or
   b. a deflection apparatus is mounted movably on the illumination objective; or
   c. a deflection apparatus is mounted movably on the detection objective.

27. The optical apparatus according to claim 14, wherein the optical apparatus is produced by retrofitting a scanning microscope or a confocal scanning microscope.

\* \* \* \* \*